US011191806B2

(12) United States Patent
Farber et al.

(10) Patent No.: US 11,191,806 B2
(45) Date of Patent: Dec. 7, 2021

(54) POLYMYXIN-BASED PHARMACEUTICAL COMPOSITION FOR TREATING INFECTIOUS DISEASES

(71) Applicants: Boris Farber, Brooklyn, NY (US); Ilya Ruvimovich Kleyn, Brooklyn, NY (US); Artur Viktorovich Martynov, Kharkov (UA)

(72) Inventors: Boris Farber, Brooklyn, NY (US); Ilya Ruvimovich Kleyn, Brooklyn, NY (US); Artur Viktorovich Martynov, Kharkov (UA)

( * ) Notice: Subject to any disclaimer, the term of this patent is extended or adjusted under 35 U.S.C. 154(b) by 0 days.

(21) Appl. No.: 16/955,896

(22) PCT Filed: May 4, 2018

(86) PCT No.: PCT/RU2018/000290
§ 371 (c)(1),
(2) Date: Jun. 19, 2020

(87) PCT Pub. No.: WO2019/212377
PCT Pub. Date: Nov. 7, 2019

(65) Prior Publication Data
US 2021/0038680 A1  Feb. 11, 2021

(51) Int. Cl.
| | |
|---|---|
| *C12P 19/42* | (2006.01) |
| *A01N 37/18* | (2006.01) |
| *A61K 38/04* | (2006.01) |
| *A61K 38/00* | (2006.01) |
| *A61P 13/12* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/12* | (2006.01) |
| *A61K 31/045* | (2006.01) |
| *A61K 31/122* | (2006.01) |
| *A61K 31/714* | (2006.01) |
| *A61K 31/185* | (2006.01) |
| *C07K 7/62* | (2006.01) |
| *C07H 23/00* | (2006.01) |

(52) U.S. Cl.
CPC ............ *A61K 38/12* (2013.01); *A61K 31/045* (2013.01); *A61K 31/122* (2013.01); *A61K 31/185* (2013.01); *A61K 31/714* (2013.01); *C07H 23/00* (2013.01); *C07K 7/62* (2013.01); *C12P 19/42* (2013.01)

(58) Field of Classification Search
None
See application file for complete search history.

(56) References Cited

U.S. PATENT DOCUMENTS

| 2002/0042394 A1* | 4/2002 | Hogenkamp | ...... A61K 51/0491 514/53 |
| 2014/0220556 A1* | 8/2014 | Martynov | .............. G01N 33/68 435/6.1 |
| 2016/0082073 A1 | 3/2016 | Hu et al. | |

OTHER PUBLICATIONS

Gupta et al., Austin J. Pharmac. Therap. 3:1-4 (2015) (Year: 2015).*
Uberti et al., Chapter 2: Vitamin D in Oxidative Stress and Diseases, available online at https://www.intechopen.com/books/a-critical-evaluation-of-vitamin-d-basic-overview/vitamin-d-in-oxidative-stress-and-diseases, 29 pages (2017) (Year: 2017).*
Larionov et al., WIREs Comput. Mol. Sci. 1:601-619 (2011) (Year: 2011).*
Britannica Online Encyclopedia, "Polymer," Britannica Online Encyclopedia, available online at https://www.britannica.com/science/polymer, 5 pages (2020) (Year: 2020).*
Felman, "Everything you need to know about vitamin B-12," Medical News Today, available online at https://www.medicalnewstoday.com/articles/219822, 8 pages at p. 2 (2017) (Year: 2017).*
LibreTexts, "22.9: Reactions of Anhydrides," available online at https://chem.libretexts.org/@go/page/30901, 4 pages (accessed on Jun. 7, 2021) (Year: 2021).*

* cited by examiner

*Primary Examiner* — Thea D' Ambrosio
(74) *Attorney, Agent, or Firm* — Daniel M. Cohn; Howard M. Cohn

(57) ABSTRACT

Field of application: The invention relates to medicine and pharmacy and allows to obtain new pharmaceutical compositions based on polymyxin for the treatment of severe infectious diseases, but not possessing nephrotoxic properties in therapeutic doses.

Figure 1:
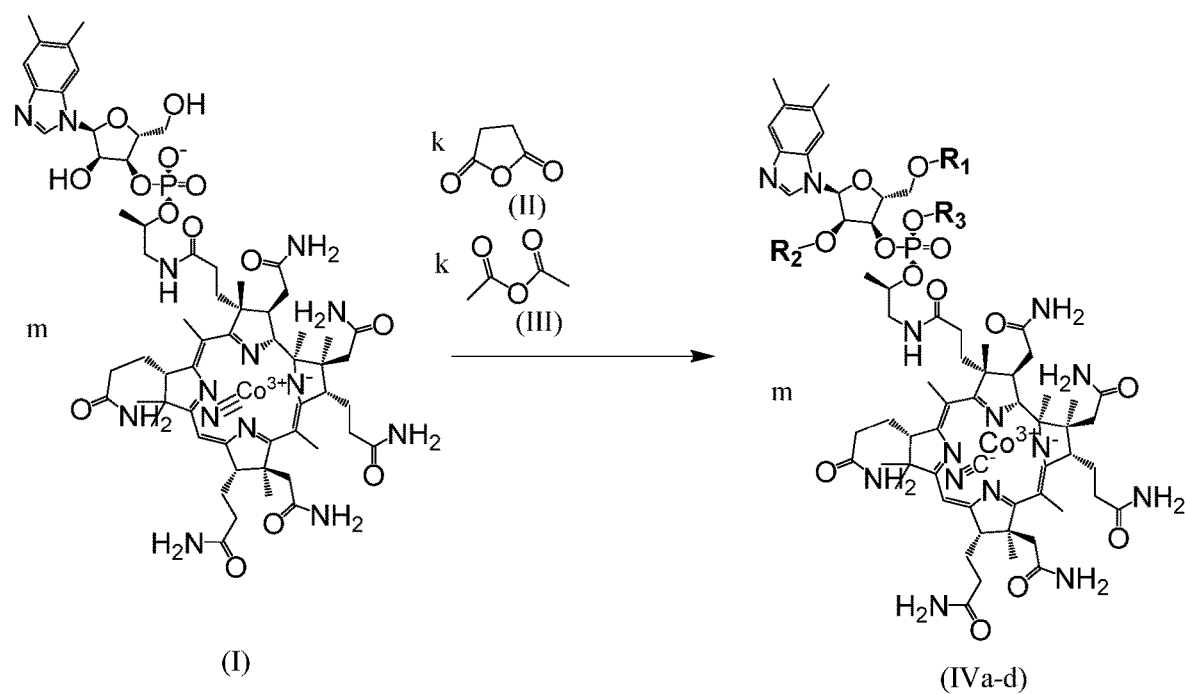

Technical result: New combined dosage forms based on the antibiotic polymyxin with low nephrotoxicity and high activity.

4 Claims, 6 Drawing Sheets

R$_1$-R$_3$= (a) H, (b)-COCH$_3$, (c) -COCH$_2$CH$_2$COOH; (d) Combinatorial sum a+b+c

POLYMYXIN-BASED PHARMACEUTICAL COMPOSITION FOR TREATING INFECTIOUS DISEASES

TECHNICAL FIELD

The invention relates to pharmacy and medicine, allows to obtain new pharmaceutical compositions based on polymyxin with significantly reduced nephrotoxicity and increased bactericidal activity.

STATE OF THE ART

Terminology

In biochemistry and pharmacology, a ligand is a chemical compound that forms a complex with a particular biomolecule (most often a protein) and produces, as a result of such binding, certain biochemical, physiological or pharmacological effects. In the case of ligand binding to a protein, the ligand is usually a small signaling molecule that binds to a specific binding site on the target protein (for example, on the receptor). The binding of a ligand to a receptor usually occurs through the forces of intermolecular interaction, such as ionic bonds, hydrogen bonds, Van der Waals forces. The binding or association of a ligand with a receptor (so-called "docking" of a ligand into a specific "niche" in the receptor) is usually reversible and short-term.

The binding of a ligand to a receptor protein changes its conformational state (three-dimensional spatial configuration). And this, in turn, can lead to a change in the functional state of the protein (for example, to the activation or inactivation of a receptor or enzyme, to the dissociation of one of the subunits of a composite protein, or, conversely, to the acquisition of the protein by binding to a ligand the ability to bind another specific ligand or another protein, either by opening the ion channel coupled to the protein, or by self-phosphorylation or other self-modification of the protein, or by the appearance of opportunities for its phosphorylation or other modification with another protein, etc.).

The term "ligand" includes enzyme substrates, antigens recognized by antibodies, and various agonists, antagonists, and inverse agonists, including endogenous ones, such as neurotransmitters, hormones, cytokines and chemokines, and inhibitors and activators of certain enzymes or regulatory proteins, and transcription factors, and exogenous, such as drugs, etc. The binding strength of a ligand to a target protein (eg, a receptor) is called "affinity", or affinity, of the ligand to a target protein (eg, a receptor). The binding strength of a ligand with a target protein is determined not only by the strength of direct interactions of the ligand with this protein (for example, a receptor), but also by the microenvironment of the protein molecule, in particular, solvent molecules present around it, which can play a dominant role in ensuring adequate intermolecular interactions of non-covalent nature between ligand and target protein (water, cell membrane lipids) and partner proteins (for example, oligomeric receptors or G-protein-coupled receptors).

In particular, an increase in the affinity of transmembrane receptors for endogenous agonists in the presence of cholesterol and sphingolipids is the reason that these receptors are usually located in certain places on the cell membrane called lipid rafts and enriched in cholesterol and sphingolipids.

The degree of attraction of the ligand for the receptor (ligand affinity for the receptor). The interaction of most ligands with their binding sites can be characterized in terms of the degree of affinity of the ligand for the receptor. In general, a high degree of affinity of one or another ligand for this particular receptor subtype is the result of a stronger intermolecular interaction between the receptor and its ligand, and vice versa—a lower degree of ligand affinity for this receptor (less attraction for this receptor) as a rule, a consequence of the lower strength of the intermolecular interaction between them.

This also means that, in general, high affinity (i.e., with high affinity, in other words, stronger) binding of the ligand to the receptor implies a longer attachment of the ligand on the receptor (and, therefore, a higher percentage of receptor occupancy at relatively low doses or concentrations of ligand).

In addition, the high affinity of binding of the ligand to the receptor often has important physiological consequences, since some of the energy of binding of the ligand to the receptor (which is naturally higher with "high affinity", with high affinity binding, which implies large force of intermolecular interaction) can be used to change the spatial configuration of the receptor, which, in turn, can lead to activation or, conversely, deactivation of the receptor and to the opening of the ion channel associated with the receptor or to a change in the behavior (increase or decrease in activity) associated with the receptor enzyme or regulatory protein.

Therefore, a having a higher affinity for the receptor, ligand is more likely to be physiologically and pharmacologically active (i.e., exhibiting one or another degree of internal agonistic activity, with whatever sign it may be—an agonist or an inverse agonist). However, this is not guaranteed—high-affinity "neutral antagonists", or rather, agents close to neutral antagonists, that is, having very low modulus internal agonistic activity, close to zero, but nevertheless exhibiting a high or very high degree of receptor affinity, affinities for it also exist.

Two agonists with a similar degree of receptor affinity (similar affinity). A receptor ligand, which can bind to a receptor, changes the spatial configuration of this receptor in such a way that it leads to its activation, and, as a result, can cause one or another physiological or biochemical cell response (to be the trigger of such a response)—called an agonist in relation to this receptor.

The binding of an agonist to a receptor can be characterized both from the point of view of how large the maximum physiological response that can be obtained by stimulating the maximum available number of receptors by a given specific agonist ("internal agonistic activity"), and from the point of view of what molar concentration this agonist is required to elicit a physiological response of one or another force ("dose-response curve"), and from the point of view of what molar concentration of this agonist is required in order to induce a physiological response of 50% of the maximum achievable for a given agonist ("Half maximum effective concentration", EC50).

Therefore, the determined and measured value of EC50 is precisely the quantitative characteristic of the measure of the affinity of an agonist for a receptor (a measure of its affinity for it). If we measure the concentration that is required to obtain 50% of the "maximum achievable physiological response in general", and not 50% of the maximum achievable for this particular agonist (taking as the maximum achievable, that is, 100%, the maximum effect of the endogenous agonist), then we get the EC50 value, which depends both on the agonist affinity value (its degree of affinity for the receptor) and on the ratio of its internal agonistic activity to the internal agonistic activity of the endogenous agonist, taken as 100%.

Thus, the determined EC50 will be a quantitative measure of not only affinity, but the molar activity of a substance (its "potency"), which is a function of both affinity (affinity for the receptor) and the internal agonistic activity ("receptor efficiency") of this ligand. Therefore, high affinity (with high attraction) affinity binding of the ligand to the receptor means that a relatively low concentration of the ligand is required to ensure full (maximum possible for a given receptor system) occupation of the binding sites of this ligand at the receptors and induce the maximum physiological response for this ligand (value which depends on the "internal agonistic activity" of the ligand). That is, the lower the Ki value characterizing the affinity of binding of the ligand to the receptor, the more likely is the formation of a chemical bond between the ligand molecules and the receptor molecules as a result of an accidental collision of molecules during Brownian motion (since there is greater intermolecular interaction force between them). A greater strength of the intermolecular interaction also means a longer average retention time of the ligand at the receptor (a longer lifetime of the non-covalent chemical bond). Conversely, low affinity binding (with low affinity for the receptor), i.e., a high Ki value, means that to achieve maximum occupancy of all available binding sites and elicit the maximum physiological response possible for this particular agonist, relatively high concentrations of this ligand are required. This also means that the formation of a chemical bond between a given ligand and a receptor as a result of an accidental collision of molecules during Brownian motion is less likely for a less affinity agonist (having a lower affinity for the receptor), since the intermolecular interaction strength is less between them and it is less specific. And the average retention time of the ligand at the low affinity receptor (having a low affinity for the receptor) is shorter, it releases the receptor faster and dissociates faster from this connection. A higher concentration for the low affinity ligand is necessary precisely because it increases the likelihood of an "accidental collision" of the low affinity ligand molecules with the receptor and the likelihood of a chemical bond between them.

Ligands that bind to receptors, however, cannot or almost cannot activate the receptor (or rather, do so with a negligible probability) and, accordingly, they themselves cannot and do not cause a physiological response of the receptor system, but only prevent the binding of both agonists and inverse agonists, and the physiological response to them, are called antagonists. Ligand binding to the receptor is often characterized in terms of what concentration of ligand is required in order to occupy 50% of all available receptor binding sites—the so-called IC50. The IC50 value is associated with the dissociation constant Ki, but differs from it. It also differs from the EC50 value, since occupying 50% of the available receptors does not necessarily lead to the production of 50% of the maximum physiological response for a given agonist, or 50% of the maximum physiological response "in general" (IC50 can be either more or less EC50, depending on the particular regulation of a particular physiological receptor system, there are both receptor systems in which occupying a relatively small number of receptors produces a great physiological effect, and, conversely, systems in which to create a significant physiological effect you need to take a large percentage of available receptors, and the dependence of the physiological effect on the percentage of receptor occupancy, as well as on the dose of the agonist, does not have to be linear at all).

If both ligands are present at the same time, then a higher percentage of the high affinity (having a higher affinity for the receptor) ligand will be associated with available receptor binding sites, compared to the less affinity ligand.

This mechanism explains, in particular, why carbon monoxide (II) even in low concentrations can compete with oxygen for binding to hemoglobin, being a higher affinity (having a greater affinity for hemoglobin) "agonist" of this transport protein, and why this often leads to carbon monoxide poisoning.

The affinity of ligand binding to the receptor (the degree of affinity of the ligand for the receptor) is most often determined using the method of displacing a labeled radioactive ligand (called a "hot ligand") with a test ligand (called a "cold" or "test" ligand). The experiments on homologous competitive binding of the ligand to the receptor are experiments in which the "hot" (labeled with a radioactive label) and "cold" (unlabeled) ligand are the same chemical substance and they compete with each other for accessible binding sites with receptor. There are also methods without the use of a radioactive label, such as surface plasmon resonance, double polarization interferometry. These methods make it possible to determine not only the affinity (degree of affinity) of an agonist for a receptor, but also the kinetics of its association and dissociation due to binding to a receptor, and in the case of double polarization interferometry, also configuration changes of a receptor caused by binding of an agonist to it. 5 Recently, a method of microthermophoresis has also been developed. This method allows you to determine the binding affinity without imposing any restrictions on the molecular weight of the ligand. To analyze the data on the kinetics of ligand binding to the receptor and on its affinity, methods of statistical mechanics are used, in particular, the calculation of the so-called "Configuration integral." Affinity for receptors (affinity) and molar activity ("potency") of the ligand.

The degree of affinity of a ligand for receptors, or the so-called "affinity" of a ligand for receptors, by itself it does not yet determine the molar activity (general "potency") of one or another ligand. The molar activity (potency) of a substance is the result of a complex interaction between its 15 degree of affinity for receptors and its internal agonistic activity (in other words, its receptor potency). Internal agonistic activity (receptor effectiveness) is a quantitative characteristic of the ability of a given ligand to elicit a particular biological response after binding to the receptor, and a measure of the magnitude of the biological response it elicits, as a percentage of the maximum possible biological response, which is taken as the maximum stimulation by an endogenous agonist (100%). Depending on the nature, character, sign and magnitude modulo the biological response caused by the ligand, it is classified either as an agonist or even a superagonist, or as a partial agonist, or as a neutral antagonist, or as an inverse agonist.

Selective and Non-Selective Ligands

Selective ligands tend to only clinically/physiologically relevant concentrations clinically/physiologically significant bind to a fairly limited set of receptor subtypes (not all of these subtypes will be receptors for the same endogenous ligand). At the same time, non-selective ligands tend to significantly bind in relevant concentrations to a fairly wide range of receptor subtypes (often to different endogenous ligands) and, thereby, produce a wider range of clinical, biochemical and physiological effects, both desirable and often unwanted side effects.

Ligand selectivity is a fairly conventional and relative concept, since there are very few truly selective ligands that bind to only one receptor subtype in the entire range of "reasonable", clinically achievable human concentrations, and even fewer ligands capable of maintaining 100% selectivity in those concentrations, which can be created in experiments on animals, and especially in vitro.

Often, the apparent relative selectivity of a ligand is lost with increasing dose or concentration (that is, at higher concentrations or doses, it begins to interact with other subtypes of receptors), and this is of great clinical importance (for example, high doses of a selective agonist of opioid buprenorphine receptors are capable of significantly depress respiration and cause euphoria, since selectivity is lost compared with morphine; similarly, high doses of selective β-blockers can cause bronchospasm, as selectivity to the β1 subtype is lost, and high doses of β2-adrenostimulants can also cause tachycardia in addition to eliminating bronchospasm; high doses of atypical antipsychotics like risperidone and olanzapine can cause extrapyramidal side effects, same like typical antipsychotics).

A measure of the relative selectivity of a ligand is the ratio of its affinity to the "desired", "main" receptor subtype (for example, to D2, in the case of antipsychotics), and to the receptor subtype closest to the next in order of magnitude—that is, the value of the ratio Ki (1)/Ki (2).

Higher affinity for the "desired" type of receptors, highly active ("more potent") compounds are often, but not always, also more selective, at least in low concentrations (the use of which, again, becomes possible precisely due to higher affinity of the compound for the receptor and greater activity of the compound). Thus, an important task of experimental and clinical pharmacology is the development of new, higher affinity (with higher attraction for the receptor) and more active ("more potent") in relation to certain types of receptors, compounds. Bivalent ligands consist of two connected molecules, each of which is a ligand for a particular subtype of receptors (the same or different), and due to the spatial structure, both parts of the molecule are able to simultaneously bind to two parts of a "compound" homo- or heterodimeric receptor complex. Bivalent ligands are used in scientific research to detect and study receptor homo- and heterodimeric complexes and study their properties. Bivalent ligands are usually large molecules and tend to not possess the properties necessary for drugs, such as convenient pharmacokinetics (acceptable bioavailability, convenient clinical use, acceptable half-life, etc.), low allergenicity and acceptable toxicity and the level of side effects, which makes them, as a rule unsuitable or minimally suitable for use in clinical practice, outside research laboratories. A privileged structure is a structural part of a molecule, a radical, or a chemical element that is or which is often statistically repeated among already known drugs of a given pharmacological class, among already known ligands of this type or subtype of receptors or known inhibitors of this enzyme, or among some other isolated by some common features of a specific subset of already known biologically active compounds.

These statistically distinguished privileged elements of the chemical structure can be further used as the basis for the development of new biologically active compounds or new drugs with similar or, possibly, even improved properties compared to the starting compounds, and even for the development of entire libraries of such compounds. Sometimes such structures are called pharmacophores. Typical examples are tricyclic structures of different chemical structures as part of tricyclic antidepressant molecules, or the existence of chemically similar whole subclasses of antipsychotics, such as butyrophenone derivatives (haloperidol, spiperone, droperidol, etc.), indole derivatives (reserpine, carbidine, etc.), phenothiazine derivatives (chlorpromazine, perphenazine, etc.).

An ensemble or supramolecular ensemble is a term from supramolecular chemistry. The objects of supramolecular chemistry are supramolecular ensembles built spontaneously from complementary, i.e., having geometrical and chemical correspondence of fragments, similar to spontaneous assembly of complex spatial structures in a living cell (Steed J. V., Atwood J. L. Supramolecular chemistry.—M.: Academic Book, 2007). Due to the fact that when synthesizing from one molecule of cyanocobalamin in the presence of two modifiers, 20 different derivatives are synthesized, intermolecular ionic and hydrogen bonds are necessarily formed between their molecules. Such supramolecular structures have a significantly higher biological activity than the original vitamin. The experiment confirmed a higher affinity of such a structure for renal megalin than unmodified cyanocobalamin or individual substituted derivatives. We used a combinatorial mixture of cyanocobalamin derivatives in the form of a supramolecular ensemble without separation into separate components.

Simultaneous combinatorial modification with two modifiers—if a multifunctional molecule is used in the combinatorial synthesis reaction—in our case, cyanocobalamin with three groups available for simultaneous modification, two modifying agents, for example, acetic anhydride and succinic anhydride, are immediately introduced into the reaction. The reaction produces a mixture of acylated derivatives in different positions—acetyl-succinyl derivatives of cyanocobalamin.

STATE OF THE ART

As a result of the search for the etiological antigen for Hayman nephritis, which is an experimental model of membrane nephropathy, Kerjaschki D. and Farquhar M. G. gp330 membrane cell protein was identified in 1982 (Kerjaschki D., Farquhar M. G., 1982, Proc. Natl. Acad. Sci. U.S.A., 79, 5557-5561). In 1994, Saito A. et al. Established the complete primary structure of rat gp330 and called it megalin, since this protein turned out to be the largest cloned membrane protein of vertebrates (Saito A. et al., 1994, Proc. Natl. Acad. Sci. USA, 91 9725-9729).

Megalin Expression Site

Megalin is also known as glycoprotein 330 (gp330) and protein 2, coupled to the low density lipoprotein receptor (LRP-2). This is a glycoprotein with a molecular weight of approximately 600 kDa, which is expressed in epithelial cells of the proximal tubules of the kidneys, in other tissues and cells, for example, in type II alveolar cells, in the male testes, in the uterine endometrium, in the placenta, in the epithelium of the inner ear, in the kidney epithelium, in the germinal vitellarium and in the neural ectoderm (see Christensen El, Willnow, T E, 1999, J. Am. Soc. Nephrol. 10, 2224-2236; Juhlin C., Klareskog L. et al., 1990, J. Biol. Chem. 265, 8275-8279; and Zheng G, McCluskey R T et al., 1994, J. Histochem. Cytochem. 42, 531-542). In the kidneys, megalin acts as an endocytosis receptor associated with endocytosis by protein reabsorption, etc. in the proximal tubule before urinary excretion. After that, reabsorption proteins, etc. destroyed by lysosomes (see Mausbach A. B., Christensen E. I., 1992, Handbook of Physiology: Renal Physiology, Windhager, editor, New York, Oxford University Press, 42-207).

The nucleotide sequence of megalin. Megalin is a glycoprotein that is most often expressed in mammals on the epithelial membrane of the proximal renal tubule. The coding sequence of megalin cDNA in nucleotide composition is identical to the sequence of human megalin cDNA with gene number U04441, disclosed in Korenberg, J. R. et al. (1994), or the human megalin cDNA sequence with gene number U33837, disclosed in Hjaeln, G., et al. (1996) (see Korenberg J. R. et al., 1994, Genomics 22, 88-93; and Hjalm G. et al., 1996, Eur. J. Biochem. 239, 132-137). In addition, Saito et al. (1994), rat megalin having homology with human megalin was discovered, and its cDNA coding sequence with the inventory number of the L34049 gene has already been disclosed (see Saito A. et al., 1994, Proc. Natl. Acad. Sci. USA, 91 9725-9729). Amino acid sequence and protein structure of megalin. Megalin is a gigantic cell membrane protein consisting of 4655 amino acids (human megalin) and 4660 amino acids (rat megalin). The molecular weight derived from the amino acid sequence is approximately 520 kDa, but may exceed 600 kDa when the sugar chain is included (see Saito A. et al., 1994, Proc. Natl. Acad. Sci. USA, 91, 9725-9729) Megalin belongs to the LDL receptor gene family, whose giant extracellular region has four functional domains, and this extracellular region is connected to the thin intracellular region through a single transmembrane region. Megalin is represented mainly in the clathrin fossa in the renal glomerulus (in rats) or on the epithelial luminal membrane (luminal and basement membranes of the glomerular epithelium cells) of the proximal renal tubule, type II alveolar cells, epididymal cells, thyroid gland, and additional thyroid glands, on the membrane of the yolk sac, in the inner ear, in the small intestine, on the chorioidea proper and is associated with the entry into the cells of various ligands and their metabolites (see Farquhar M G et al., 1995, J. Am. Soc. Nephrol 6, 35-47; and Christensen El et al., 2002, Nat. Rev. Mol. Cell. Biol. 3, 256-266). In mice with megalin knockout, diseases and disorders such as low molecular weight proteinuria, disorders of bone metabolism, respiratory failure, brain malformations and others are observed (see Willnow T E et al., 1996, Proc. Natl. Acad. Sci. USA, 93 8460-8464). Nematodes (C. elegans) also have a megalin homolog, which has been suggested to be of biological importance (see Yochem J. et al., 1993, Proc. Natl. Acad. Sci. U.S.A., 90, 4572-4576). The value of megalin as a cause of nephritis.

Megalin, the main etiological antigen of experimental membrane nephropathy (Hayman nephritis), is an epithelial phagocytic receptor, the biological and pathological role of which is established. Animal models have long been used to elucidate the mechanism of development of human membranous nephropathy, and Hayman rat nephritis is a model of membrane nephropathy. Hayman's analysis of jade has advanced further than analysis of any other model. Saito A. et al. revealed the results of the analysis of the pathological epitope and ligand-binding domain of Hayman nephritis, and also demonstrated the main antigenic region of megalin and the functional megalin domain, which provide the main contribution to ligand binding (see Kerjaschki D. et al., 1992, Proc. Natl. Acad. Sci. USA, 89, 11179-11183; Saito A., Farquhar M G et al., 1996, Proc. Natl. Acad. Sci. USA, 93, 8601-8605; Yamazaki H., Farquhar M G et al., 1998, J Am. Soc. Nephrol. 9, 1638-1644; and Orlando R A, Farquhar M G et al., 1997, Proc. Natl. Acad. Sci. USA, 94, 2368-2373)

Various megalin ligands. Megalin is most abundantly expressed in vivo on the luminal side of the epithelial cells of the proximal tubules of the kidneys. In human kidneys, megalin expression is not observed in any other places except the epithelial cells of the proximal tubules, including glomeruli. Megalin incorporates various ligands (e.g., low molecular weight proteins or drugs) that are glomerularly filtered into cells through endocytosis, megalin transports them to lysosomes, and they reappear on the cell surface through recycling (see Farquhar M G et al., 1995, 20 J. Am Soc. Nephrol. 6, 35-47; and Christensen El et al., 2002, Nat. Rev. Mol. Cell. Biol. 3, 256-266). In addition, megalin is associated with transcytosis from the luminal side to the basal side of the membrane. Megalin is also associated with the uptake and metabolism of binding proteins such as vitamins A, B12 and D (see Christensen E. I. et al., 2002, Nat. Rev. Mol. Cell. Biol. 3, 256-266). Christensen and Willnow have demonstrated that megalin mediates the reabsorption of three vitamin-carrier proteins: Vitamin D-binding protein (DBP), Retinol-binding protein (RBP), and Transcobalamin (TC), as well as their associated vitamins, i.e. (OH) vitamin 25D3, vitamin A (retinol) and vitamin B12 (see Christensen El, Willnow T E, 1999, J. Am. Soc. Nephrol. 10, 2224-2236).

Saito A. et al. Demonstrated that adipocyte-secreted leptin, which is elevated in the blood of obese patients, is incorporated and metabolized by the proximal tubule epithelial cells as megalin ligand (see Saito A., Gejyo F. et al., 2004, Endocrinology 145, 3935-3940). Adipocytes, i.e. accumulated visceral fats, lead to combined pathological conditions, i.e. metabolic syndrome. Leptin, which is an adipocytokine secreted by adipocytes, is elevated in the blood of patients with metabolic syndrome. Researchers believe that the kidney is the organ in which leptin circulating in the blood is most likely to accumulate, and this leptin plays a nephropathic role (see Tarzi R M, Lord G M et al., 2004, Am. J. Pathol. 164, 385-390).

The so-called leptin receptor is also found in the area between the proximal tubule and the collecting tubule, located below the region of megalin functioning. Saito A. et al. Conducted an experiment with epithelial cells extracted from the yolk sac of a rat embryo (L2 cells), in which megalin was expressed at a high level, and found that the incorporation of glucose-derived enhanced glycosylation (AGE) end products with a radioisotope tag 125I in L2 cells can be largely suppressed by antibodies against megalin. Thus, they demonstrated that megalin is associated with the metabolic pathway of such inclusion (see Saito A., Gejyo F. et al., 2003, J. Am. Soc. Nephrol. 14, 1123-1131). The interaction of the end products of enhanced glycosylation (AGE) with glycosylated and modified proteins in the Maillard reaction was indicated as a mechanism for the development of diabetic nephropathy.

The low molecular weight AGE present in the blood is filtered by the renal glomeruli, and is reabsorbed and metabolized by the epithelial cells of the proximal tubule. If nephropathy progresses further, then the high molecular weight AGE, which accumulates in the epithelial cells of the proximal tubules and creates an excessive metabolic load, is also glomerularly filtered. Further, Saito A. et al. Also demonstrated that megalin is associated with the incorporation into cells (in addition to glucose) of AGE obtained from methylglyoxal, glyceryldehyde or glycolaldehyde. In addition, the metabolic syndrome is often complicated by hepatopathy, for example, fatty degeneration of the liver. Liver-type fatty acid binding 5 proteins (L-FABP), abundantly present in the liver, are released into healthy blood in healthy people. With hepatopathy, the release of L-FABP increases, which leads to an increase in their level in the blood. Saito A. et al. Also demonstrated that blood L-FABP is rapidly filtered by renal glomeruli and reabsorbed by proximal tubule epithelial cells through megalin (see Takeda T., Gejyo F., 10 Saito A. et al., 2005, Lab. Invest. 85, 522-531).

Functional Protein Interacting with Megalin

In order to clarify the mechanism of megalin transport in cells, a search was made for adapter molecules that bind to the intracellular domains of megalin, during which various proteins were identified, for example, Dab2, ANKRA, MAGI-1, GAIP, GIPC, Galphai3, MegBP and ARH (see Oleinikov A V et al., 2000, Biochem. J. 347, 613-621; Rader K., Farquhar M G et al., 2000, J. Am. Soc. Nephrol. 11, 2167-2178; Patrie K M, Margolis B. et al., 2001, J. Am. Soc. Nephrol. 12, 667-677; Lou X., Farquhar M G et al., 2002, J. Am. Soc. Nephrol. 13, 918-927; Petersen H H, Willnow T E, 2003, J. Cell. Sci. 116, 453-461; and Takeda T., Farquhar M G et al., 2003, Mol. Biol. Cell. 14, 4984-4996). Through these molecules, megalin is associated with endocytosis and transcytosis, as well as related signal transduction. In addition, megalin functions conjugatively with the receptor of the cell membrane, i.e. with cubilin in the epithelial cells of the proximal tubules, due to which it is additionally involved in the processes of incorporation of various ligands into cells (see Saito A. et al., 1994, Proc. Natl. Acad. Sci. USA, 91, 9725-9729). For example, cubilin is a receptor that directly binds to transferrin, albumin, endogenous vitamin B12, etc., and megalin is indirectly included in their endocytosis. It is also known that megalin interacts in the epithelial cells of the proximal tubules with isoform 3 of the exchanger Na+−H+(NHE3) (see Biemesderfer D. et al., 1999, J. Biol. Chem. 274, 17518-17524). NHE3 is an antiporter that plays an important role in the reabsorption of Na+; in addition, NHE3 affects the incorporation of ligands by megalin (see Hryciw D. H. et al., 2004, Clin. Exp. Pharmacol. Physiol. 31, 372-379). Megalin may also be involved in the inactivation and metabolism of NHE3. In the early stages of diabetic nephropathy or nephropathy associated with metabolic syndrome, glomerular filtration becomes excessive. Enhanced reabsorption of Na+in the proximal tubules was found to be the main cause (see Vallon V. et al., 2003, J. Am. Soc. Nephrol. 14, 530-537), with NHE3 in this case playing a key role. and inactivation and metabolization of NHE3 by megalin also appears to play a role in these processes (see Hryciw D H et al., 2004, Clin. Exp. Pharmacol. Physiol. 31, 372-379).

The importance of megalin function found in experiments using models of uremia and models of organ regeneration. As described above, megalin is involved in the absorption of various low molecular weight proteins by the epithelial cells of the proximal renal tubules and in their metabolism. If the pathological condition progresses to the stage of renal failure, the metabolic mechanism is disturbed, as a result of which low molecular weight proteins accumulate in the blood and tissues as uremic proteins. A typical example is β2-microglobulin (β2-m), which can cause dialysis amyloidosis in patients receiving long-term dialysis (see Gejyo F., Schmid K. et al., 1985, Biochem. Biophys. Res. Commun. 129, 701-706).

The aforementioned AGE is also considered to be the cause of arteriosclerosis or organ failure due to its accumulation in the blood of patients with renal failure or prolonged dialysis, and AGE is considered as a uremic type protein (Henle T., Miyata T., 2003, Adv. Ren. Replace Ther. 10, 321-331). Further, leptin accumulates in the blood of patients receiving dialysis, therefore it is believed that it is involved in malnutrition and an immune disorder. Tabata Y. and Gejyo F. et al. Disclosed the effects and efficacy of uremic protein metabolism models using megalin functions (see Saito A., Tabata Y., Gejyo F. et al., 2003, J. Am. Soc. Nephrol. 14, 2025-2032 and document WO 02/091955).

That is, megalin-expressing cells are transplanted in vivo as a building proteins, and low molecular weight proteins are leaking out from the peripheral blood vessels 5 (blood vessels of newborn) are inserted into the cells using megalin for subsequent metabolism. Megalin-expressing cells used for transplantation (i.e., L2 cells derived from the yolk sac epithelium) incorporate and metabolize β2-m with megalin (see Saito A., Tabata Y., Gejyo F. et al., 2003, J. Am. Soc. Nephrol. 14, 2025-2032). Renal failure was induced by the removal of both kidneys in a nude mouse, which underwent subcutaneous transplantation of L2 cells, after which the incorporation of cells into the tissue mass and into organs into which cells with β2-m labeled with the 125I isotope were transplanted was measured by intraperitoneal injection. As a result, it was found that the cell mass into which L2 cells were transplanted incorporated the 125I labeled isotope more intensively than other organs, and the excretion of β2-m labeled 125I was significantly increased in the group in which L2 cells were transplanted compared to a control group in which L2 cell transplantation was not performed (see Saito A., Tabata Y., Gejyo F. et al., 2003, J. Am. Soc. Nephrol. 14, 2025-2032)

Polymyxin and megalin. (Lisnyak, Yu. V.2015. Annals of Mechnicov Institute, (3), 8-24.) The recent interest in polymyxins in the world is caused by the significant spread of nosocomial infections resistant to a wide range of modern antimicrobial agents and the lack of new effective antibiotics against gram-negative bacteria. According to experts, the absence of such antimicrobial agents can lead to a return to the pre-antibiotic era.

At the same time, most gram-negative bacteria are sensitive to polymyxins, and the formation of resistance to these cationic lipopeptides is slow and much less common compared to other antibiotics. In the 70s of the 20th century, polymyxins were abandoned due to cases of nephrotoxicity and the appearance of drugs with fewer side effects. However, when the use of β-lactams, aminoglycosides or quinolones against extremely multiresistant strains of gram-negative bacteria, including *P. aeruginosa, A. baumannii* and *K. pneumoniae*, becomes ineffective, polymyxin B and colistin remain the last resort in the treatment of these infections.

The group of polymyxin peptides includes several chemically different compounds (polymyxins AE, M, S and others). In clinical practice, only polymyxins B and E (colistin) are used. Polymyxin B (polymyxin, PmB) is a cyclic lipo-decapeptide (FIG. 1) containing six residues of α, γ-diaminobutanoic acid (Dab): MOA-Dab1-Thr2-Dab3-cycle [Dab4-Dab5-D-Phe6-Leu7-Dab8-Dab9-Thr10]. Seven amino acids of polymyxin form a macrocycle (cycle [Dab4-Dab5-D-Phe6-Leu7-Dab8-Dab9-Thr10]), and three amino acids (Dab1-Thr2-Dab3) make up the linear portion connecting the macrocycle to the terminal residue of methyl octanoic acid (MOA). The macrocycle is formed by an additional peptide bond between Thr10 and the γ-amino group of the Dab4 residue. The N-terminal residue of Dab1 polymyxins Na-acylated with a fatty acid such as 6-methyl-octanoic acid (PmB1), 6-methyl-hexanoic acid (PmB2), octanoic acid (PmB3), etc. The only structural difference between colistin (colistin, polymyxin E, PmE) and polymyxin B is the amino acid D-Leu at position 6 instead of D-Phe in polymyxin B. Polymyxin B and colistin contain five free amino groups (as part of Dab) and, accordingly, five positive charges under physiological conditions.

The "return" of polymyxins to clinical practice stimulated further in-depth studies of their toxicity. In the last decade, the toxicity of polymyxin B and colistin has been carefully checked by modern methods (taking into account the correct use, chemical purity and homogeneity of the preparations) and was not as high as was believed in the past. Nevertheless, it can still significantly complicate therapy, reduce its effectiveness and even lead to its complete cessation. Therefore, the creation of less toxic derivatives of polymyxin remains a very urgent task. Over the past decade, several research groups have focused on developing less toxic polymyxin derivatives. In particular, N. Sakura et al. Created polymixin derivatives Ser2-Dap3-PmB (2-10), Dap3-PmB (3-10) and Ser3-PmB (3-10), the acute toxicity of which (LD50) is about 10 times lower than that of polymyxin B1, and activity against *Pseudomonas aeruginosa* remains approximately at the level of polymyxin B. Vaara M. et al. synthesized less nephrotoxic derivatives of polymyxin NAB7061, NAB739 and NAB740, whose renal clearance was, respectively, 28, 53 and 378 times higher than colistin, and affinity for the membrane of the brush strip of the rat kidney epithelium was 2-3 times lower than that of gentamicin, and 5-6 times lower than polymyxin B1.

The search for non-toxic derivatives of polymyxin as a whole is conducted empirically, without involving any molecular mechanisms of its nephrotoxicity and/or structural models of the polymyxin-target interaction. A prerequisite for the directed search for such derivatives is the knowledge of the molecular mechanisms of the nephrotoxicity of polymyxins, based on detailed information about the peculiarities of the intermolecular interactions of polymyxins with their targets for nephrotoxicity.

It is known that the nephrotoxic effect of polymyxin is due to their accumulation in the epithelial cells of the proximal tubule of the kidney, and it will persist there for a long time, causing damage to the kidney: polymyxin accumulation in increasing amounts in the lysosomes leads to swelling and, ultimately, to rupture of the lysosomes and the release of polymyxins into the cytosol where their non-specific binding causes acute tubular necrosis. In this case, the main factor in the accumulation of these antibiotics in the kidney is their interaction with megalin (previously called gp330 glycoprotein), a giant cell surface receptor that is most abundant in the apical membrane of the proximal tubule of the kidney. Thus, this receptor can be a unique target for creating polymyxin antibiotics with minimized nephrotoxicity.

The weakening of the binding of polymyxins to megalin can be a new preventive measure against polymyxin-induced nephrotoxicity. Megalin is a trans-membrane glycoprotein that plays a central role in the endocytotic function of the epithelial cells of the proximal tubule of the kidney; megalin also involved in signal transduction in these cells. Megalin is localized in the clathrin caveoles of the epithelium of the proximal tubule of the kidney and functions as an endocytotic receptor that binds a very wide range of substances. Ligands that bind to megalin (there are more than 30), are represented by several groups of compounds: proteins included in the lipoprotein metabolism; proteases and protease-inhibitor complexes; matrix proteins; intracellular proteins; growth factors and other groups (including lactoferrin, rhinovirus, complement C3, gentamicin, polymyxin, etc.).

Megalin is a member of the low density lipoprotein receptor (LDLR) gene family. The LDLR family is a class of structurally homologous membrane receptors consisting of modular structures (domains) and represented in mammals by the seven main glycoproteins: low density lipoprotein receptor (LDLR); very low density lipoprotein receptor (VLDLR); apolipoprotein-E receptor 2 (ApoER2 or LRP8); multiple epidermal growth factor (MEGF7); LDLR-linked protein 1 (LRP1); LDLR-linked protein 1 b (LRP1b) and LDLR-bound protein 2 (LRP1) or megalin (Megalin). Megalin is the largest representative of this family, its mass is about 600 kDa. The amino acid sequence of rat megalin contains 4460 amino acids and contains a 25-amino acid N-terminal signal peptide sequence, a 4400 amino acid extracellular region, a 22-amino acid single-pass transmembrane domain, and a 213-amino acid C-terminal cytoplasmic tail. the amino acid sequences of human and rat megalin are similar by 77%. The extracellular region of megalin contains structural modules that are characteristic of all members of the LDLR 5 family—cysteine-enriched ligand-binding repeats (in the literature they are also called complement-like repeats (or domains) and are designated CR (Complement-type Repeat), growth factor repeats (EGF repeats) and β-propeller domains: As directed mutagenesis studies show, the ligand-binding CR repeat binding sites of most ligands by LDL receptors are.

The extracellular region of LDLR (the smallest member of the LDLR family) contains 7 ligand-binding repeats that form one cluster, while the extracellular regions of LRP and megalin contain, respectively, 31 and 36 ligand-binding repeats distributed in four clusters (clusters I-IV) Each of the CR domains consists of approximately 40 amino acid residues. The first data on the three dimensional organization of CR repeats were obtained by N. L. Daly et al. Using nuclear magnetic resonance spectroscopy (NMR spectroscopy) for repeating CR1 and then CR2 from human LDLR (PDB codes 1 LDL and 1 LDR, respectively). It was found that these modules contain 3 disulfide bonds, as well as such basic elements of the secondary structure of the protein as β-hairpins and β-bends. Next, the crystal structure of the CR5 domain from human LDLR was determined with a resolution of 1.7 Å (PDB code 1AJJ), which showed for the first time that the module contains Ca2+ion, which is octahedrally coordinated by negatively charged residues of aspartic (Asp) and glutamine (Glu) acids and carbonyl groups of the core, forming a pocket around a calcium ion.

Later it was shown that the Ca2+ion is necessary for the correct folding of the polypeptide chain and support the structural integrity of the module. Structural data for megalin are currently quite limited: only one structure of the 12th CR domain of rat megalin and one structure of the 10th CR domain of human megalin (as well as its complex with gentamicin) determined in the NMR method is known. However, the structures of all seven CR domains of LDLR and several CR domains of LRP receptors are known, which were obtained both for individual modules using NMR spectroscopy or X-ray crystallography, and for their pairs.

All structures of these CR domains have the same type of folding of the polypeptide chain: a short antiparallel β-sheet, two loops stabilized by disulfide bonds between CysI-CysIII, CysIV-CysVI cysteines and linked by CysII-CysV disulfide bridge. The N-terminal loop is additionally stabilized by the antiparallel β-sheet, and the C-terminal loop is additionally stabilized by the interactions of the residues coordinated around the Ca2+ion. The similar folding of the polypeptide chain and the similar three-dimensional organization of CR domains is a consequence of the homology of their amino acid sequences containing conserved residues of aspartic (D) and glutamic (E) acids and a conserved arrangement of six cysteine residues (C).

The preferred binding sites of many important ligands by representatives of the LDLR family are ligand-binding repeats. As an analysis of the available structural data on the interaction of members of the LDLR family with their cationic ligands shows, the recognition site on the receptor is a common (universal) structural motif and contains three acidic (negatively charged) residues of aspartic acid coordinated by the Ca2+ion (the so-called DXDXD motif) and one hydrophobic residue. The ligand recognition/binding site is positively charged lysine residues. The binding is carried out mainly due to electrostatic interactions between positively charged ligand residues and negatively charged aspartic acid residues involved in the coordination of the Ca2+ion. This lysine binding is enhanced by hydrophobic interaction between the aromatic residue of the CR module (tryptophan or phenylalanine) and the aliphatic lysine fragment. Thus, key characteristics of the binding site include: (1) coordination of calcium ion (gray dashed lines), (2) salt bridges and hydrogen bonds between residues of aspartic acid CR repeat and cationic ligand residues (blue dashed lines) and (3) hydrophobic interactions between the aromatic residue of the ligand-binding repeat and the aliphatic portion of lysine (brown dashed lines).

The polymyxin binding site on its molecular target, megalin, has not yet been experimentally established, and there are also no structural models of the interaction of polymyxin with megalin at the atomic level. However, polymyxin B (like gentamicin) is known to be an effective competitive inhibitor of rat megalin binding of the RAP protein (Receptor-Associated Protein, receptor-bound protein). RAP is a chaperone that binds to members of the LDL receptor family and acts as a universal antagonist of their premature binding to its ligands in the endoplasmic reticulum (leading to their aggregation and degradation), ensuring normal expression of these receptors on the cell surface for their endocytotic function. The polymyxin binding site on its molecular target, megalin, has not yet been experimentally established, and there are also no structural models of the interaction of polymyxin with megalin at the atomic level. However, polymyxin B (like gentamicin) is known to be an effective competitive inhibitor of rat megalin binding of the RAP protein (Receptor-Associated Protein, receptor-bound protein). RAP is a chaperone that binds to members of the LDL receptor family and acts as a universal antagonist of their premature binding to its ligands in the endoplasmic reticulum (leading to their aggregation and degradation), ensuring normal expression of these receptors on the cell surface for their endocytotic function.

Competitive inhibition involves both the structural similarity of the inhibitor and the substrate (at least, the structural similarity of their molecular fragments that interact with the receptor), and the same binding site on the receptor. And structural models of the interaction of RAP protein with LDL receptors at the atomic level are known. And in these complexes, also positively charged NH3-groups of gentamicin interact with three negatively charged residues of aspartic acid of the CR10 domain, i.e., with the structural DXDXD motif found for other CR modules. Thus, there is reason to believe that the DXDXD structural motifs of the ligand-binding CR domains of megalin (FIG. 17) are also binding sites for polymyxins, and their cationic Dab groups (analogues of lysine residues) are molecular fragments of polymyxins that interact with the receptor.

As shown by studies by Vaara M. et al., NAB-derivatives of polymyxin having only three positive charges located within the macrocycle of the molecule (charged residues Dab5, Dab8 and Dab9) are not only effective antibacterial agents, but also have significantly lower nephrotoxicity than the original polymyxin containing five positive charges (charged residues Dab1, Dab3, Dab5, Dab8 and Dab9). Moreover, their renal clearance was tens and hundreds of times higher than that of colistin, and their affinity for the membrane of the brush strip of the rat kidney epithelium was 5-6 times lower than that of polymyxin B1, that is, polymyxin derivatives with weakened interaction with the target had the best pharmacokinetic indicators.

Thus, the level of nephrotoxicity of polymyxin and its derivatives correlates with the features of their molecular structure and, as a consequence, with the features of their intermolecular interactions with megalin. A new derivative of polymyxin/colistin, which will not be recognized by megalin, is expected to have significantly less nephrotoxicity. What are the features of intermolecular interactions of polymyxin with megalin ? What are the structural prerequisites for differences in the interaction of polymyxin and its NAB derivatives with megalin? The answers to these questions will be given by ongoing studies of the structural and functional relationships of polymyxins and their molecular targets for nephrotoxicity.

Recently, the structures of the complexes of the ligand-binding domain of human megalin CR10 with another cationic antibiotic, gentamicin, which also has an adverse nephrotoxic effect, were determined by NMR spectroscopy and molecular modeling (docking). Megalin is a unique target for the creation of polymyxin antibiotics with minimized nephrotoxicity. The weakening of the binding of polymyxins to megalin can be a new preventive measure against polymyxin-induced nephrotoxicity.

Known nephrotoxicity inhibitors for aminoglycoside antibiotics [U.S. Pat. No. 4,526,888]. These inhibitors, which are patented in the composition with aminoglycoside antibiotics, include polyaspartic acid and polyaspartates in the form of salts or amides, as well as polyglutamic acid, polyglutamates and their amides. These compounds are able to protect the kidneys from the action of aminoglycoside antibiotics through their higher tropism to the kidneys.

Although these polymers did not inhibit the antimicrobial activity of aminoglycoside antibiotics, they had a number of significant drawbacks—these are semisynthetic polymers—xenobiotics with an incompletely studied metabolic mechanism, the polymer nature of these compounds when injected together with high tropism to the kidney tissue allows these compounds to accumulate in kidneys with the formation of amyloid plaques, these compounds are new xenobiotics and they are not yet approved for use. In addition, in combination with polymyxin, they have not previously been used.

A known method of suppressing the nephrotoxicity of polymyxin by combining its use with high doses of ascorbic acid (Sirijatuphat, R., Limmahakhun, S., Sirivatanauksorn, V., Nation, R L, Li, J., & Thamlikitkul, V. (2015). Preliminary clinical study of the effect of ascorbic acid on colistin-associated nephrotoxicity. Antimicrobial agents and chemotherapy, 59 (6), 3224-3232.). Significant protective activity of sodium ascorbate for injection is shown during treatment with polymyxin. The disadvantage of this method is the delayed toxicity of polymyxin, due to the lack of tropism (high affinity) of ascorbic acid for renal megalin. The mechanism of action of ascorbic acid is not associated with the inhibition of the interaction of polymyxin with megalin, but is associated with the suppression of lipid peroxidation (POL) and the release of free radicals (SR) in the kidneys. LPO and SR are the main consequence of megalin destruction, including the cascade of the nephron decay chain reaction.

Moreover, after the termination of the action of ascorbic acid, the nephrotoxicity of polymyxin manifested for a longer period of time after completion of treatment. Similar LPO and CP inhibitors, such as retinoic acid (various derivatives of vitamin A), vitamin E, melatonin, etc., although they protect the kidneys from the immediate action of polymyxin during the treatment, they are not able to protect the kidneys from the long-term "cumulated" action of polymyxin (Yousef, J M, Chen, G., Hill, Pa., Nation, R L, & Li, J. (2011). Melatonin attenuates colistin-induced nephrotoxicity in rats. Antimicrobial agents and chemotherapy, 55 (9), 4044-4049.). The cessation of LPO and SR inhibitors immediately manifests the nephrotoxic effects of polymyxin previously bound to megalin. These side effects are deprived of the high-affinity megalin ligands, which can generally prevent the interaction of polymyxin with megalin without negatively affecting the antimicrobial effect of polymyxin.

DISCLOSURE OF INVENTION

The basis of the invention is the task to develop a pharmaceutical composition based on polymyxin with reduced nephrotoxicity for the treatment of infectious diseases. The problem is solved by obtaining a pharmaceutical composition based on polymyxin for the treatment of infectious diseases, including nephroprotectors, characterized in that it contains a combination of vitamins with a supramolecular combinatorial derivative of cyanocobalamin obtained by simultaneous covalent modification of the structure of cyanocobalamin maximum five modifiers.

The composition can be made in the form for parenteral use: solutions for injection, lyophilized powder for extemporaneous use; in the form for oral administration: tablets, syrups, capsules, solutions for oral administration; in the form for transdermal use: plasters, ointments, gels, powders; in the form for rectal use: suppositories, solutions for douching; in topical form: dressings, plasters, powders, gels, powders, and also include pharmaceutically acceptable preservatives, stabilizers and excipients, including ascorbic acid, its sodium and potassium salt, melatonin, parabens, carboxymethyl cellulose, SPAN20, TWEEN80.

The composition may also include additional antibacterial substances, such as fluoroquinolones, carbapenems, macrolides.

Pharmaceutical Compositions

Various methods of preparing a patentable pharmaceutical composition (PFC) can be used. The PFC composition can be given orally or can be administered by intravascular, subcutaneous, intraperitoneal injection, in the form of an aerosol, by ocular route of administration, into the bladder, topically, and so on. For example, inhalation methods are well known in the art. The dose of the therapeutic composition will vary widely depending on the particular antimicrobial PFC administered, the nature of the disease, frequency of administration, route of administration, clearance of the agent used from the host, and the like. The initial dose may be higher with subsequent lower maintenance doses. The dose can be administered with a frequency of once a week or once every two weeks, or divided into smaller doses and administered once or several times a day, twice a week, and so on to maintain an effective dose level. In many cases, a higher dose will be needed for oral administration than for intravenous administration, PFCs can be included in many therapeutic compositions. More specifically, the PFCs of the present invention can be incorporated into pharmaceutical compositions in combination with suitable pharmaceutically acceptable carriers or diluents, and can be incorporated into preparations in solid, semi-solid, liquid or gaseous forms, such as capsules, powders, granules, ointments, creams, foams, solutions, suppositories, injections, forms for inhalation use, gels, microspheres, lotions and aerosols. As such, the administration of the compounds can be carried out in various ways, including oral, buccal, rectal, parenteral, intraperitoneal, intradermal, transdermal, intratracheal administration and so on. The PFCs of the invention can be distributed systemically after administration or can be localized using an implant or other composition that holds the active dose at the site of implantation. The PFCs of the present invention can be administered alone, in combination with each other, or they can be used in combination with other known compounds (e.g., fluoroquinolones, carbopenems, and so on). In pharmaceutical dosage forms, nephroprotective agents may be administered in the form of their pharmaceutically acceptable salts. The following methods and excipients are given as examples only and are in no way limiting. For oral preparations, the compounds can be used alone or in combination with suitable additives for the manufacture of tablets, powders, granules or capsules, for example, with conventional additives such as lactose, mannitol, corn starch or potato starch; with binding agents, such as crystalline cellulose, cellulose derivatives, gum arabic, corn starch or gelatins; with disintegrants such as corn starch, potato starch or sodium carboxymethyl cellulose; with lubricants 10 such as talc or magnesium stearate; and, if desired, with diluents agents, moisturizing agents, preservatives and flavoring agents.

PFCs should be included in injectable compositions by dissolving, suspending or emulsifying them in an aqueous or non-aqueous solvent, such as vegetable or other similar oils, synthetic aliphatic acid glycerides, esters of higher aliphatic acids or propylene glycol; and, if desired, with conventional additives such as solubilizers, isotonic agents, suspending agents, emulsifiers, stabilizers and preservatives. PFCs can be used in an aerosol composition for inhalation administration.

The compounds of the present invention can be incorporated into suitable pressure propellants such as dichlorodifluoromethane, propane, nitrogen and the like. In addition, PFCs can be incorporated into suppositories by mixing with a variety of bases, such as emulsifying bases or water-soluble bases. The compounds of the present invention can be administered rectally using a suppository. A suppository may contain excipients, such as cocoa butter, carboax, and polyethylene glycols, which melt at body temperature but are solid at room temperature.

Standard dosage forms for oral or rectal administration, such as syrups, elixirs and suspensions, where each unit dose, for example, a teaspoon, tablespoon, tablet or suppository, may contain a predetermined amount of a composition containing one or more compounds of the present invention. Similarly, unit dosage forms for injection or intravenous administration may contain the compound of the present invention in a composition in the form of a solution in sterile water, normal saline, or another pharmaceutically acceptable carrier.

Implants for the sustained release of compositions are well known in the art. Implants are made in the form of microspheres, plates, and so on with biodegradable or non-biodegradable polymers. For example, lactic and/or glycolic acid polymers form a degradable polymer that is well tolerated by the host. An implant containing the PFC according to the invention is positioned close to the focus of the pathology, so that the local concentration of the active agent is increased compared to other areas of the body.

As used herein, the term "unit dosage form" refers to physically discrete units suitable for use as single doses for human and animal subjects, each unit containing a predetermined number of compounds of the present invention, which, according to calculations, is sufficient to provide the desired effect together with a pharmaceutically acceptable diluent, carrier or excipient. The descriptions of the unit dosage forms of the present invention depend on the particular compound used, and the effect to be achieved, and the pharmacodynamics of the compound used in the host. Pharmaceutically acceptable excipients, such as excipients, adjuvants, carriers or diluents, are generally available.

In addition, pharmaceutically acceptable excipients are generally available, such as pH adjusting agents and buffering agents, tonicity agents, stabilizers, wetting agents and the like. Typical doses for systemic administration range from 0.1 pg to 1000 milligrams per kg of subject body weight per administration. A typical dose may be a single tablet for administration from two to six times a day, or one capsule or sustained release tablet for administration once a day with a proportionally higher content of the active ingredient.

The effect of prolonged release may be due to the materials of which the capsule is made, dissolving at different pH values, capsules providing a slow release under the influence of osmotic pressure or any other known controlled release method. It will be clear to those skilled in the art that dose levels may vary depending on the particular compound, the severity of the symptoms, and the subject's predisposition to side effects. Some of the specific compounds are more potent than others. Preferred doses of this compound can be readily determined by those skilled in the art in a variety of ways.

The preferred method is to measure the physiological activity of PFC. One of the methods of interest is the use of liposomes as a vehicle for delivery. Liposomes fuse with the cells of the target region and ensure the delivery of liposome contents into the cells. The contact of the liposomes with the cells is maintained for a time sufficient for fusion using various methods of maintaining contact, such as isolation, binding agents and the like. In one aspect of the invention, liposomes are designed to produce an aerosol for pulmonary administration. Liposomes can be made with purified proteins or peptides that mediate membrane fusion, such as Sendai virus or influenza virus and so on.

Lipids may be any useful combination of known liposome forming lipids, including cationic or zwitterionic lipids, such as phosphatidylcholine. The remaining lipids will usually be neutral or acidic lipids, such as cholesterol, phosphatidylserine, phosphatidylglycerol and the like. To obtain liposomes, the method described by Kato et al. (1991) J. Biol. Chem. 266: 3361.

Briefly, lipids and a composition for incorporation into liposomes containing peptides are mixed in a suitable aqueous medium, suitably in a salt medium, where the total solids content will be in the range of about 110 wt. %. After vigorous stirring for short periods of approximately 5-60 seconds, the tube is placed in a warm water bath at approximately 25-40° C. and this cycle is repeated approximately 5-10 times. The composition is then sonicated for a suitable period of time, typically approximately 1-10 seconds, and optionally further mixed with a vortex mixer. Then the volume is increased by adding an aqueous medium, usually increasing the volume by about 1-2 times, followed by agitation and cooling. The method allows you to include in the liposomes both polymyxin and patented nephroprotectors.

BRIEF DESCRIPTION OF THE DRAWINGS

FIG. 1. Scheme for the chemical synthesis of a supramolecular derivative of combinatorial modified cyanocobalamin.

FIG. 2. HPLC (Milichrom A-02) of cyanocobalamin (I), gradient A solution: 0.5 M lithium perchlorate/0.1 M perchloric acid, solution B: acetonitrile (B from 5% to 100%)

FIG. 3. HPLC (Milichrom A-02) of the combinatorial supramolecular derivative of cyanocobalamin (IVd), gradient solution A: 0.5 M lithium perchlorate/0.1 M perchloric acid, solution B: acetonitrile (B from 5% to 100%)

FIG. 4. HPLC (Milichrom A-02) triacetyl-cyanocobalamin (IVb), gradient solution A: 0.5 M lithium perchlorate/0.1 M perchloric acid, solution B: acetonitrile (B from 5% to 100%)

FIG. 5. HPLC (Milichrom A-02) trisuccinyl-cyanocobalamin (IVc), gradient solution A: 0.5 M lithium perchlorate/0.1 M perchloric acid, solution B: acetonitrile (B from 5% to 100%)

FIG. 6. Direct inhibition of colistin accumulation with cyanocobalamin (IVd) and cholecalciferol from the Polyfro composition

EMBODIMENTS OF THE INVENTION

The following examples do not limit the possibility of using other methods of obtaining the composition of this invention, are presented only for the purpose of explaining the implementation of the claims.

Example 1. Synthesis of a Supramolecular Combinatorial Derivative of Cyanocobalamin (SCDC)

20 mM cyanocobalamin (I) is dissolved in 10 ml of dioxane, 21 mM succinic anhydride (III) and 21 mM acetic anhydride are added, the solution is stirred and heated under reflux for 20 minutes. The solution was poured into ampoules and lyophilized to remove solvent and acetic acid. The supramolecular combinatorial derivative (IVd) or SCDC is used to obtain pharmaceutical compositions, study the structure, and determine the biological activity. FIG. 1 shows a synthesis scheme for combinatorial derivatives of quercetin.

One Source Cyanocobalamin Molecule Contains 3 Hydroxyl Groups Available for Modification, Including One Phosphate.

Calculations of the number of moles of modifiers are carried out according to the combinatorics formulas:

$$m=4\times(3\times2^{n-2}-1);k=n\times(2^n-1),$$

where m is the number of different derivatives of molecules in the combinatorial mixture and the number of moles of cyanocobalamin for the reaction;

n—the number of hydroxyl groups available for modification, including one phosphate in the structure of cyanocobalamin (n=3);

k is the number of moles of each modifier.

Thus, having only one initial quercetin molecule and two modifiers after combinatorial synthesis, we obtain 20 combinatorial derivatives with different degrees of substitution, different positions of the substituents and different permutations of the modifier residues, not just as a mixture, but as a difficult to separate supramolecular structure.

Modifiers—succinic anhydride or acetic anhydride can be entered both simultaneously and sequentially—or first inject succinic anhydride, warm the mixture under reflux for 20 minutes, and then add acetic anhydride and also warm the mixture for another 20 minutes. Similarly, in this reaction, maleic anhydride, aconitic anhydride, glutaric, phthalic anhydride and acetic anhydride, formic acid ethyl ester, monochloroacetic acid, propiolactone, ethylene oxide and other low molecular chlorides can be used as one of the modifiers instead of succinic anhydride.) For the purpose of studying the biological activity of the synthesized substances, various derivatives with different ratios of modifiers were obtained (Table 1).

Figure 3:
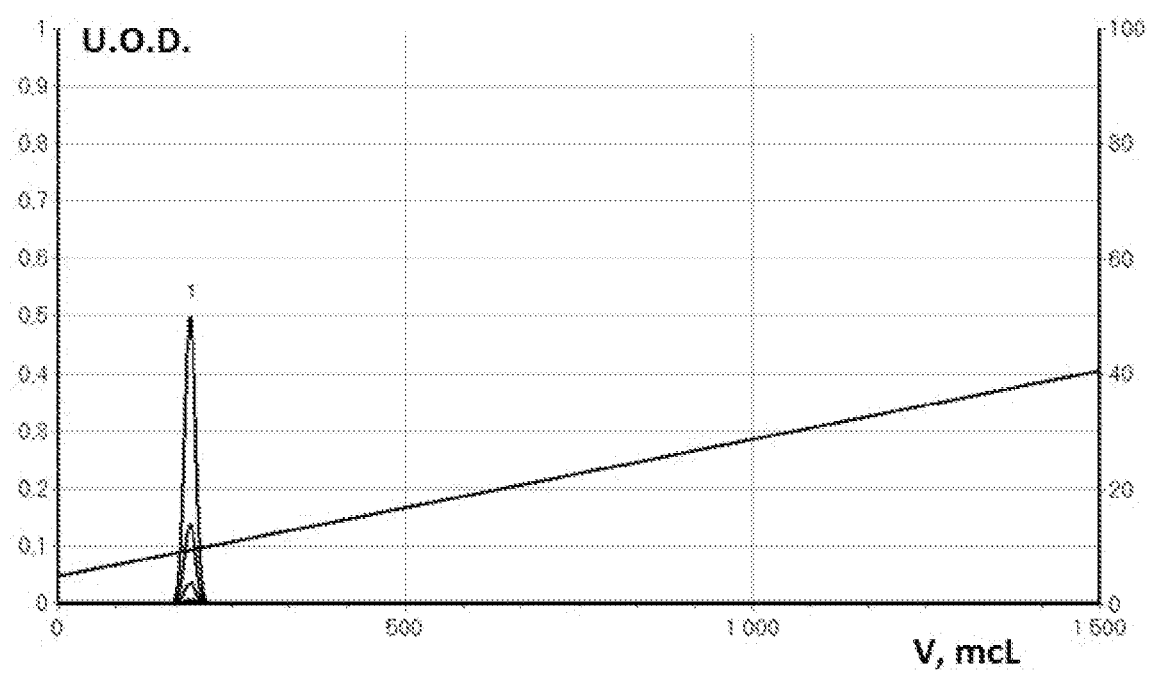
Figure 4:
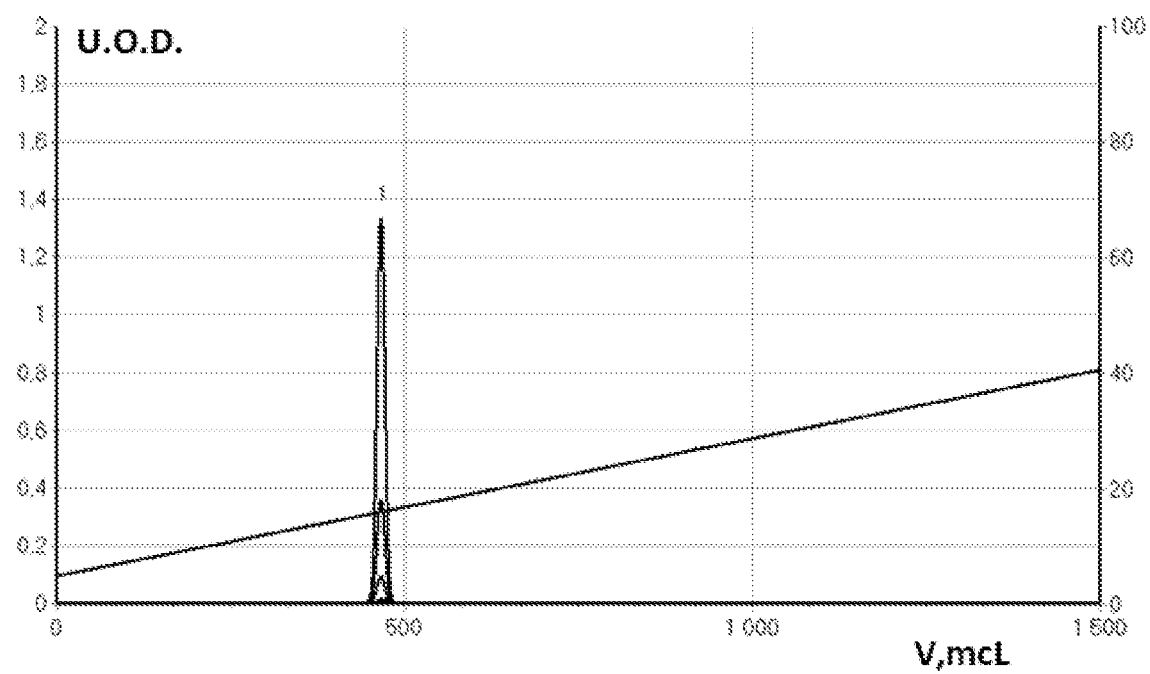
Figure 5:
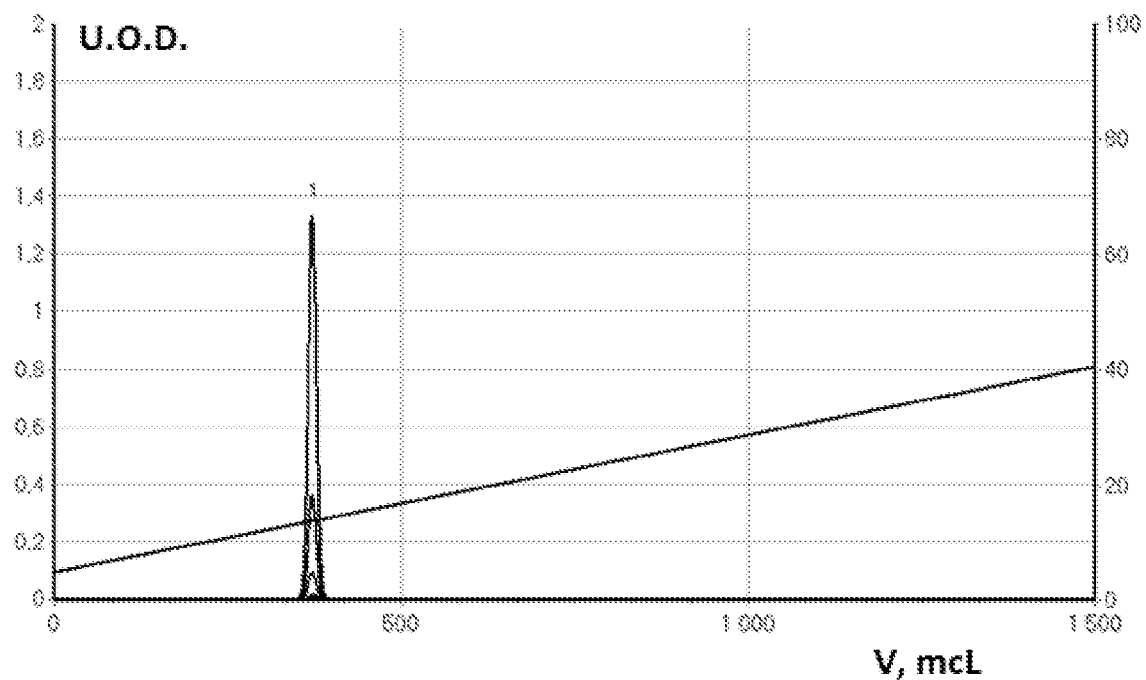

For the HPLC, a Milichrom A-02 microcolumn chromatograph in a gradient of acetonitrile (5-100%)/0.1 M perchloric acid+0.5 M lithium perchlorate was used. The combinatorial derivative of SCDC (IVd) in the chromatogram (FIG. 3) gave one clear broadened peak and did not separate into components, although the retention time was practically the same as pure cyanocobalamin, while its completely substituted derivatives had different retention volumes (FIG. 4., FIG. 5). This testified to the fact that complex supramolecular structures were formed between different combinatorial derivatives (in our case there are 20 of them), which were not separated chromatographically. This combinatorial derivative (SCDC) (IVd) also behaves similarly when separated in a thin layer (acetonitrile:water) and gives only one band, which does not coincide with any of the derivatives obtained.

Table 1 shows the results of screening of cyanocobalamin derivatives with different ratios of modifiers as a substrate of renal megalin (on the example of megalin of rat kidney homogenate). The initial cyanocobalamin is known to be a substrate/ligand of renal megalin with a moderate degree of interaction and an average affinity for megalin for absorption (IA=52%). The test was carried out by a micromethod in Eppendorf tubes on the ability of cyanocobalamin derivatives to bind to megalin: after centrifugation, the bound derivative together with megalin remained in the sediment, and the percentage of the remaining unreacted cyanocobalamin derivative in the supernatant was determined using HPLC on a Milichrom A-02 liquid chromatograph. The relative concentration in % relative to the original is shown in table 1.

TABLE 1

The ability of megalin to bind different derivatives of cyanocobalamin SCDC

| No p/p | The molar ratio of reagents * | | | % bound derivative |
|---|---|---|---|---|
| | m | k1 | k2 | |
| 1. | 20 | 84*** | 84*** | 5 |
| 2. | —//— | 42 | 42 | 12 |
| 3. | —//— | 21 | 21 | 98 |
| 4. | —//— | 17 | 17 | 71 |
| 5. | —//— | 13 | 13 | 71 |
| 6. | —//— | 9 | 9 | 70 |
| 7. | —//— | 5 | 5 | 67 |
| 8. | —//— | 3 | 3 | 58 |
| 9. | —//— | 2 | 2 | 57 |
| 10. | —//— | 1 | 1 | 57 |
| 11. | —//— | 0 | 0 | 52 |
| 12. | —//— | 42 | 0 | 56 |
| 13. | —//— | 21 | 0 | 67 |
| 14. | —//— | 17 | 0 | 71 |
| 15. | —//— | 13 | 0 | 66 |
| 16. | —//— | 9 | 0 | 62 |
| 17. | —//— | 5 | 0 | 57 |

TABLE 1-continued

The ability of megalin to bind different derivatives of cyanocobalamin SCDC

| No p/p | The molar ratio of reagents * | | | % bound derivative |
|---|---|---|---|---|
| | m | k1 | k2 | |
| 18. | —//— | 3 | 0 | 58 |
| 19. | —//— | 2 | 0 | 57 |
| 20. | —//— | 1 | 0 | 56 |
| 21. | —//— | 0 | 1 | 57 |
| 22. | —//— | 0 | 2 | 55 |
| 23. | —//— | 0 | 3 | 57 |
| 24. | —//— | 0 | 5 | 50 |
| 25. | —//— | 0 | 9 | 59 |
| 26. | —//— | 0 | 13 | 37 |
| 27. | —//— | 0 | 17 | 27 |
| 28. | —//— | 0 | 21 | 15 |
| 29. | —//— | 0 | 42 | 10 |
| 30. | —//— | 0 | 84*** | 6 |
| 31. | —//— | 84*** | 0 | 7 |
| 32. | —//— | 42 | 1 | 11 |
| 33. | —//— | 21 | 2 | 23 |
| 34. | —//— | 17 | 3 | 46 |
| 35. | —//— | 13 | 5 | 57 |
| 36. | —//— | 9 | 9 | 59 |
| 37. | —//— | 5 | 13 | 55 |
| 38. | —//— | 3 | 17 | 34 |
| 39. | —//— | 2 | 21 | 21 |
| 40. | —//— | 1 | 42 | 11 |

* m is the number of moles of cyanocobalamin in the combinatorial synthesis reaction; K1 is the number of moles of succinic anhydride in the reaction; K2 is the number of moles of acetic anhydride in the reaction;
*** the maximum molar ratio at which all groups in cyanocobalamin are replaced, exceeding this ratio leads to the fact that unreacted modifiers remain in the reaction medium - succinic anhydride and acetic anhydride.

As can be seen from table 1, only with the calculated ratio of components, when the maximum number of different derivatives of cyanocobalamin is formed, is a biological active and effective supramolecular structure formed (derivative 3 or SCDC or IVd in FIG. 1.), which almost completely (98%) binds to renal megalin. Other derivatives either did not differ from unmodified cyanocobalamin (52%) in their ability to bind to megalin, or were significantly less active. This indicates that with the optimal ratio of modifiers when all possible derivatives are formed in the solution (21 variations of the derivatives of zmanocobalamin with different permutations and arrangements in the substituents), a more complex supramolecular "quasi-lowering" structure with other properties and greater pharmacological activity is formed.

Figure 2:
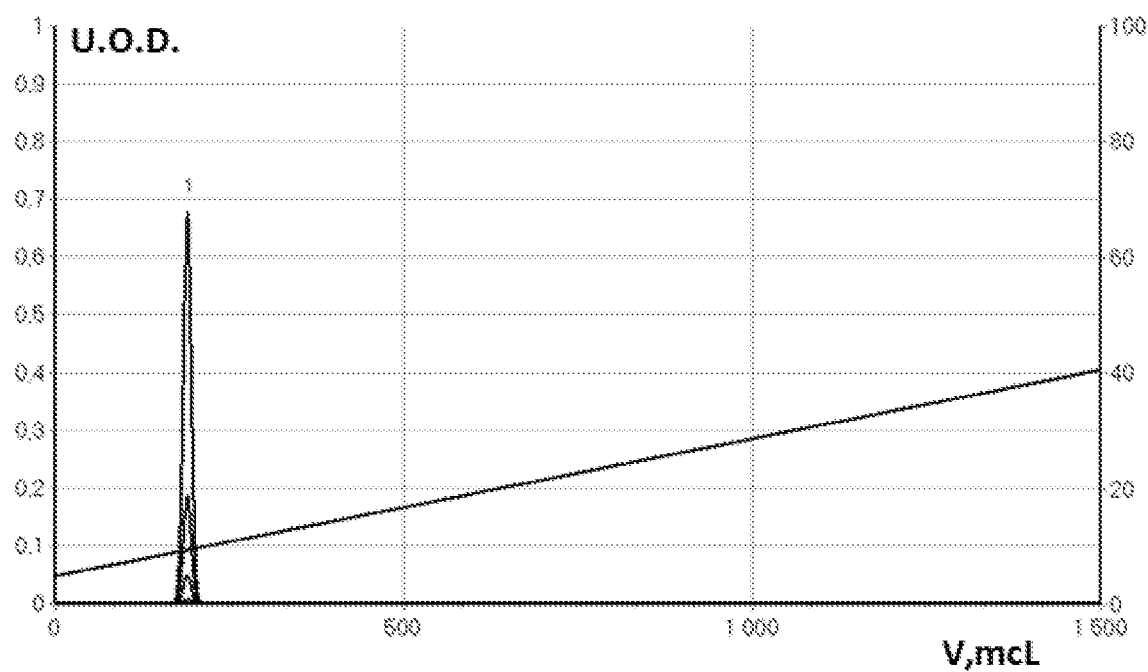

In FIG. 2 shows the chromatogram of the initial cyanocobalamin (I), a combinatorial modified with two anhydrides (IVd) (FIG. 5). FIGS. 3-4 show HPLC chromatograms of two derivatives: fully succinylated (IVc) and fully acetylated cyanocobalamin (IVb), respectively, as control samples (No. 30 and No. 31 in Table 1). As can be seen from the graphs, the retention volume of the combinatorial derivative practically does not differ from the initial cyanocobalamin, but differs from fully modified derivatives. In addition, at the same concentration of cyanocobalamin, the peak area and width of its base are larger, which indicates that these are derivatives of cyanocobalamin and that there are several of them. The differences between the retention volume (I), (IVb) and (IVc) indicate the completion of the reaction of complete succinylation and acetylation in the structure of cyanocobalamin, respectively, and also that all these derivatives inside the complex (IVd) form a complex supramolecular structure.

Fully succinylated and fully acetylated cyanocobalamin absorbed megalin only 6% and 7%, respectively. Thus, the IVd derivative obtained in accordance with combinatorial calculations is a fundamentally new supramolecular structure that has significantly different properties both from unmodified cyanocobalamin (No. 11 in Table 1) and from fully modified derivatives (No. 30 and No. 31 in Table 1) This structure cannot be separated using gradient HPLC, and the UV spectra of all derivatives practically coincide, although the retention time is different. This indicates the formation of new structures with a covalent bond based on cyanocobalamin, and at the same time, these structures together form a complex supramolecular structure similar to cyclodextrin complexes.

Example 2 Preparation of Polymyxin-Based Pharmaceutical Compositions with Nephroprotectors This object is achieved in that the pharmaceutical composition with antimicrobial activity contains an antibiotic polymyxin, contains cyanocobalamin, SCDC and cholecalciferol blocking its nephrotoxic effect, as well as targeted additives that contribute to the formation of dosage forms. According to the invention, SCDC, the main active agent is administered in an amount of 0.5-20%, polyvinylpyrrolidone is used as a solubilizer, sodium laurisulfate is a surfactant, the main components of the pharmaceutical composition, when a certain technological operation due to mechanochemical interaction form a complex with the studied pharmaceutical and pharmacological properties.

Moreover, in the pharmaceutical composition SCDC and cholecalciferol is contained in an amount of from 2 to 7%. Instead of cholecalciferol, another nephroprotector can be used: vikasol, pantothenic acid, nicotinamide adenine dinucleotide. While SCDC in the composition may be contained in an amount of from 10 to 40%. The substances are pre-dissolved in ethanol together with lecithin or TWEEN-80, and ethanol is distilled off by heating or under vacuum. In addition, as the target additives, the solubilizer polyvinylpyrrolidone in the amount of 10-50% and the surface-active agent sodium lauryl sulfate in the amount of 0.25-10% were selected.

The task is also achieved by the fact that in the method for producing a pharmaceutical composition with antimicrobial activity according to the invention, preliminarily polymyxin with nephroprotective agents and target additives are mixed, compacted, milled, the resulting mixture is mixed with pharmaceutically acceptable excipients, dry or wet granulation of the mixture is carried out, then the granulate is filled hard gelatin capsules or pressed and the tablets are coated with a polymer film. According to the invention, the developed method for producing a pharmaceutical composition allows to obtain dosage forms with a complex pharmaceutical composition in the form of coated tablets or capsules 10 containing components in such a 40 quantitative range, in %:
Polymyxin 5-25%
SCDC/cholecalciferol 10-40%
Fillers up to 100%

The three active substances of the new pharmaceutical composition were combined in it, taking into account the knowledge about their pharmacological and therapeutic properties obtained with the use of monopreparations based on their substances. The selected target additives, due to their physicochemical properties, contribute to the solubilization of active substances and their sufficiently high dissolution in the physiological aqueous medium of the gastrointestinal tract.

The combination of three active substances with different physicochemical properties in one dosage form is a rather difficult task for pharmacy. The solution of the problem in technical terms was carried out by the consistent development of the manufacturing technology of the pharmaceutical composition and in accordance with the pharmacopoeial methods of its research.

First of all, the pharmaceutical development of the pharmaceutical composition began with an assessment of the physicochemical properties of polymyxin, SCDC and cholecalciferol, primarily focusing on their ability to emulsify in aqueous media so that these active substances have maximum bioavailability when the drug is administered orally under physiological conditions of the stomach substances possible only with the use of auxiliary substances with properties. It was possible to achieve high solubility using solubilizers and surfactants.

Such solubility modulators are polyvinylpyrrolidone (povidone, PVP) and sodium lauryl sulfate (LSS), TWEEN-80 and lectin, the quantitative values of their introduction into the pharmaceutical composition were determined during the pharmaceutical development of the composition, focusing on the solubility profiles of the samples, performing the solubility test. Studying the kinetics of dissolution of samples of the pharmaceutical composition, both granules for capsules and tablets, with variable mass values of PVP, LSS, TWEEN-80 and lecithin, their optimal ratio with polymyxin was established.

TABLE 2

Composition and ratio of ingredients in one capsule or tablet core of the pharmaceutical composition Polyfro

| No p/p | Name of ingredient | in mg | in % |
|---|---|---|---|
| 1 | 2 | 4 | 5 |
| 1 | Liposomes with cholecalciferol (LCh) | 40.00 | 20.00 |
| 2 | Polyvinylpyrrolidone K-25 | 40.00 | 20.00 |
| 3 | Polymyxin | 25.00 | 12.50 |
| 4 | Microcrystalline cellulose | 80.00 | 40.00 |
| 5 | TWEEN-80 | 10.00 | 5.00 |
| 6 | SCDC | 3.00 | 1.50 |
| 6 | Magnesium stearate | 2.00 | 1.00 |
| | Content of capsule or tablet core: | 200.00 | 100.00 |

To ensure the physicochemical stability of the complex, the weight ratio between LSS and PVP should be in the range 1:1-1:3. It should be noted that these mass values of PVP are also sufficient to increase the solubility of the Polymyxin substance due to the formation of the corresponding complex compound. The povidones used in their molecular weights differ as follows: K90—1,000,000; K25—30000; C17—10000. Considering the characteristics of the dissolution kinetics of the complex of quercetin with PVP, a sufficient amount of LSS, a surfactant, was selected to facilitate the rapid and uniform wetting of the surface of the complex granulate.

To ensure the physicochemical stability of the complex, the weight ratio between LSS and PVP should be in the range 1:1-1:3. It should be noted that these mass values of PVP are also sufficient to increase the solubility of the Polymyxin substance due to the formation of the corresponding complex compound. The povidones used in their molecular weights differ as follows: K90—1,000,000; K25—30000; C17—10000. Considering the characteristics of the dissolution kinetics of the complex of quercetin with PVP, a sufficient amount of LSS, a surfactant, was selected to facilitate the rapid and uniform wetting of the surface of the complex granulate.

To ensure the physicochemical stability of the complex, the weight ratio between LSS and PVP should be in the range 1:1-1:3. It should be noted that these mass values of PVP are also sufficient to increase the solubility of the Polymyxin substance due to the formation of the corresponding complex compound. The povidones used in their molecular weights differ as follows: K90—1,000,000; K25—30,000; C17—10000. Considering the characteristics of the dissolution kinetics of the complex of quercetin with PVP, a sufficient amount of LSS, a surfactant, was selected to facilitate the rapid and uniform wetting of the surface of the complex granulate.

This also reflected in the acceleration of the dissolution of the complex in the initial periods of time and, thus, could create optimal conditions for the absorption by the walls of the stomach of the soluble form of polymyxin. With significant hydrophobicity of the surface of the DN crystals, these selected auxiliary substances—PVP and VLF, also contributed to the solubility of this substance, and thereby could increase the bioavailability of this NSAID. A positive effect on the solubility of liposomes and polymyxin is also exerted by a selected amount of PVP and LSS, as evidenced by solubility profiles.

All samples of the pharmaceutical composition, starting with a complex of active substances—polymyxin and liposomes with cholecalciferol with PVP and LSS, were obtained under consecutive technological operations by dry or wet granulation of the ingredients of the complex and auxiliary substances. The prepared granules were used to fill the capsules or they were tabletted and the solubility of these dosage forms was examined in accordance with the Pharmacopoeia Dissolution test. The solubility characteristics of Polyfro in the pharmaceutical composition indicated a significantly higher solubility of these active ingredients compared to the solubility of individual substances.

In the course of pharmaceutical development, a sample of a pharmaceutical composition of a certain composition was made (see Table 2), called by the authors "Polyfro" and found application in studies of pharmacological properties.

The pharmaceutical composition of the given composition obtained in accordance with the dry granulation technology includes: mixing the active substances with excipients, compacting or briquetting the mixture, grinding, mixing the grinding with excipients and granulating, compressing the granulate into tablets or filling it with hard gelatin capsules.

Wet granulation technology is characterized by a granulation stage of the mixture, where instead of a compactor or press, wet granulation equipment and a dryer are used, such as a mixer granulator with agitators, such as Rota P or a granulator-dryer of a fluidized bed, such as Hurtling.

We present specific examples of the invention. The following examples illustrate the main aspects of the present invention, but should not be construed as limiting. The preparation of all samples of granules of the complex of active substances—polymyxin, SCDC, and cholecalciferol in liposomes with PVP—was carried out under the conditions of technological granulation using the dry or wet method, using dry pressing (compaction) of a mixture of active ingredients, followed by grinding of the briquetted material.

Wet granulation was carried out in granulator-dryers in a vacuum or warm running air in devices with a pseudo-boiling layer. Capsules were filled into the obtained granules or tabletted, examining the solubility of these dosage forms by the Dissolution test. The solubility characteristics of the polymyxin/SCDC/liposomal cholecalciferol system in the pharmaceutical composition indicated a significantly higher solubility of the complex of active ingredients compared with the solubility of individual substances. Thus, in the course of pharmaceutical development, a sample of the pharmaceutical composition was made, called by the inventors "Polyfro", which found, as a preparation of a certain composition, the use in research of toxic-pharmacological properties:

TABLE 3

Composition and ratio of ingredients per capsule or tablet of the Polyfro pharmaceutical composition

| No. p/p | Ingredients name | mg | % |
|---|---|---|---|
| 1 | 2 | 3 | 4 |
| 1 | * Liposomes with cholecalciferol (LH) | 40.00 | 20.00 |
| 2 | * Polyvinylpyrrolidone K-25 | 40.00 | 20.00 |
| 3 | * Polymyxin | 25.00 | 12.50 |
| 4 | Microcrystalline cellulose | 80.00 | 40.00 |
| 5 | * TWEEN 80 | 10.00 | 5.00 |
| 6 | * SCDC | 3.00 | 1.50 |
| 7 | Magnesium stearate | 2.00 | 1.00 |
| 8. | Contents of capsule or tablet core | 200.00 | 100.00 |

* these compounds together with the phosphate buffer in the % ratios were used to create a liquid injection form for in vitro and in vivo experiments.

The pharmaceutical composition of the given composition (Table 3) obtained by dry granulation technology, including mixing the active substances with excipients, compacting or briquetting the mixture, grinding and mixing it with excipients, and finally granulate it is compressed into tablets or filled with hard gelatin capsules. Wet granulation technology is characterized by the stage of granulating the mixture, where instead of a compactor or press, wet granulation and drying equipment is used, such as a granulator-mixer with agitators, type 25 Rota P or granulator-dryer, such as Huttling with a boiling layer. The following embodiments illustrate aspects of the invention, but should not be construed as limiting.

Example 3. Obtaining a Liposomal Suspension Form of Cholecalciferol for Further Production of Granulate, Tablet Mass and Tablet Forms with Polymyxin and SPPC In 80-200 ml of 60% ethanol, 2-20 g of polymyxin, 1-3 g of cholecalciferol, 1-7 g of SCDC and 20-50 g of phosphatidylcholine are dissolved, then ethanol is distilled off under vacuum, 50 ml of distilled water are added to the resulting mixture and sonicated at 44 kHz for 15-50 minutes, the resulting suspension of liposomes is dried in a freeze dryer, and the resulting powder is used as shown in the previous examples to obtain tablet forms, injection forms. The size of liposomal nanoparticles in ultrasonic emulsification is 120-300 nm. If milk powder is used instead of lecithin, the particle size will be 500-1000 nm.

A preclinical study of the pharmaceutical composition was carried out using the Polyfro sample in research tests in order to establish the full toxicological and pharmacological properties of the future drug, which could become a promising drug.

Example 4. Inhibition of the Accumulation of Polymyxin in the Kidneys

In this experiment was determined, the accumulation of colistin in the kidneys of rats after intravenous injection of Polyfro (colistin, SCDC and liposomal cholecalciferol). Concentrations of colistin (CC), SCDC/cholecalciferol (CCF) were used based on preliminary modeling (the number of binding sites in one molecule, multiplied by their number in one megalin molecule, the molecular weight of megalin and the approximate amount of megalin in one kidney and the weight of the kidney) The result was the required amount of SCDC about 2 mg/kg of weight. For CS, a subtoxic dose was selected (based on the instructions). This is an experiment on the "displacement" of polymyxin from the kidneys with a synergistic combination of SCDC/HCF. As a result, about half of the polymyxin was displaced from the kidneys by SCDC/HCF. All components of CC, SCDC/CCF were determined in the sediment of renal homogenate and supernatant by HPLC. In our opinion, the Central Committee is one of the best candidates for nephroprotective agents, which now can significantly reduce the toxicity of polymyxin in clinics. FIG. 1 shows the accumulation of colistin (A) and the concentration (B) of colistin in megalin kidneys in mice. After 45 minutes of intravenous injection of the Polyfro mixture in terms of SCDC (2 mg/kg) and colistin (0.5 mg/kg) or physical. solution in the control collected urine of rats after 180 minutes. The content of colistin in the kidneys (A) and its concentration in terms of the weight of the kidneys (µg/g) (B) are shown in FIG. 1.

Figure 6:
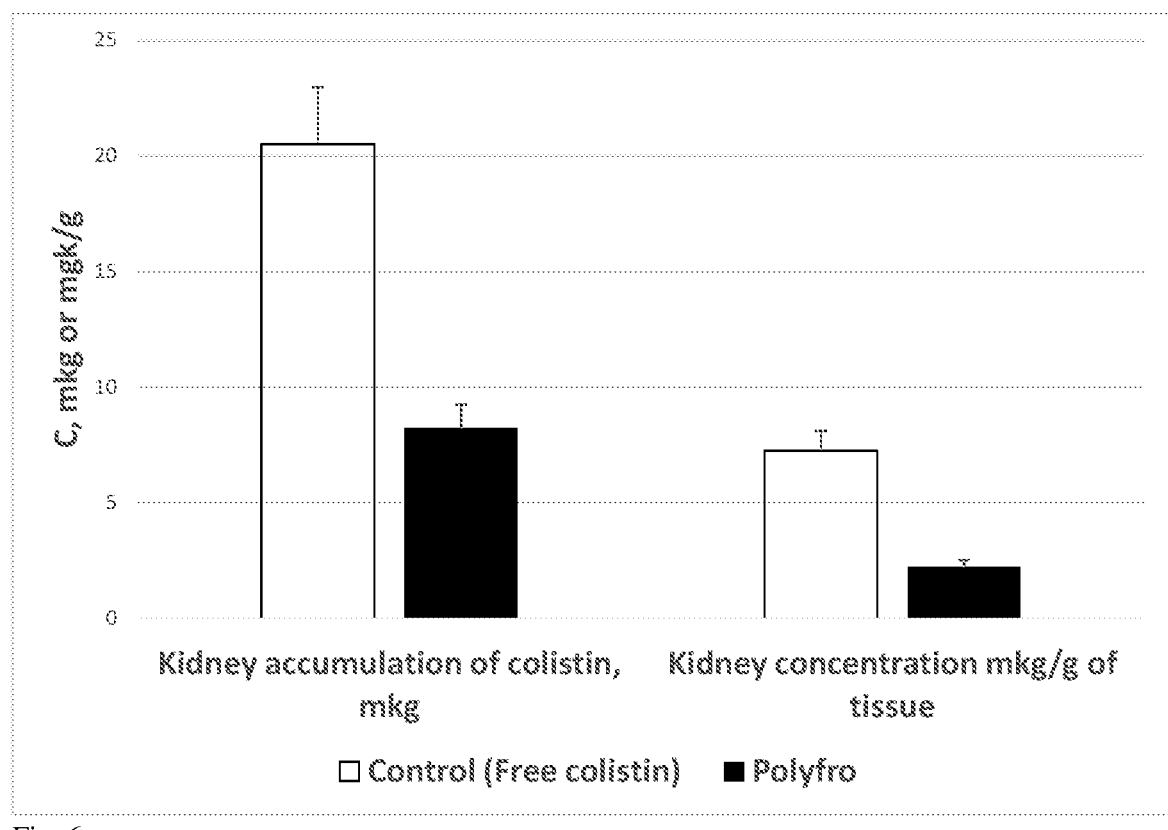

Each column shows the average value (SD) of four measurements at $P<0.05$ (against control). As can be seen from FIG. 6., the accumulation of colistin in the kidney tissues both in absolute terms and in relative terms in terms of the weight of the kidneys decreases by more than two times due to the higher affinity for megalin in SCDC and cholecalciferol. All data are statistically significant and differences between groups and controls are significant.

Table 4 presents the results of suppressing the accumulation of colistin in the tissues of the kidneys for other pharmaceutical compositions with colistin.

Example 5. Prevention of Nephroprotective Agents from Polyfro Destruction of Renal Tissue The degree of destruction of kidney tissue was determined by the concentration in the urine of acetyl-beta-glucosaminidase (N-acetyl-beta-d-glucosaminidase) (NAG) and neutrophilic gelatinase-associated lipocalin (neutrophil gelatinase-associated lipocalin) (NGAL) (Table 5).

In the same rats treated with pure colistin and Polyfro, urine parameters were studied showing the degree of renal destruction (doses of 0.5/15 mg/kg polymyxin/SCDC in Polyfro as an intravenous injection 1 time per day for 10 days). The concentrations of NGAL and NAG in urine were determined using ELISA-text systems on a StatFax303+ reader. Table 4 shows comparative data on the effect of free colistin and the Polyfro pharmaceutical composition on the degree of destruction of kidney tissue.

TABLE 5

The effect of colistin and the combined pharmaceutical composition Polyfro on the degree of destruction of the kidneys

| | The value for the experimental group: | |
|---|---|---|
| Index | Polyfro (n = 13) | Colistin (n = 15) |
| Urinary Excretion of NGAL (mcg/h) | 577* ± 18 | 775 ± 33 |
| Urinary NAG Excretion (mcg/h) | 331* ± 10 | 2578 ± 95 |

*$P < 0.05$; differences between the control and experimental groups are statistically significant As can be seen from table 5, the differences in the concentrations of NGAL and NAG between the groups where pure colistin was used and Polyfro were statistically significant, that is, SCDC/liposomal cholecalciferol effectively protect the kidneys from the negative effects of colistin. Table 6 shows similar data for other pharmaceutical compositions with polymyxin.

TABLE 4

The accumulation of polymyxin in the presence of nephroprotectors in the tissues of the kidneys

| No. p/p | Composition content | Accumulation of colistin in the kidneys mcg | Concentration of colistin in the kidney, conversion to kidney tissue in µg/g |
|---|---|---|---|
| 1 | Control (colistin) | 20.5 ± 2.5 | 8.25 ± 2.25 |
| 2 | Polifro | 7.25 ± 1.25* | 2.25 ± 1.25 |
| 3 | Colistin/Pantothenic acid/NAD | 6.25 ± 1.25* | 2.50 ± 1.25 |
| 4 | Colistin/SCDC/Vikasol | 7.25 ± 2.25* | 2.25 ± 1.25 |
| 5 | Colistin/Cholecalciferol/Vikasol | 9.50 ± 2.50* | 4.50 ± 1.50 |
| 6 | Colistin/SCDC/Pantothenic Acid | 8.50 ± 1.50* | 3.50 ± 1.50 |
| 7 | Colistin/Pantothenic Acid/Vikassol | 6.25 ± 1.25* | 2.50 ± 0.50 |
| 8 | Colistin/SCDC/NAD | 7.25 ± 1.25* | 2.25 ± 1.25 |
| 9 | Colistin/Vikasol/NAD | 8.50 ± 1.50* | 3.50 ± 1.50 |
| 10 | Colistin/Cholecalciferol/NAD | 4.50 ± 1.50* | 2.00 ± 0.50 |
| 11 | Colistin/Cholecalciferol/pantothenic acid | 7.25 ± 1.25* | 2.25 ± 1.25 |

*$P < 0.05$ As can be seen from table 4, all combinations of high affinity megalin ligands successfully prevent the accumulation of polymyxin in the megalin of the kidneys. Differences with control without nephroprotectors are statistically significant.

TABLE 6

The accumulation of polymyxin in the presence of
nephroprotectors in the tissues of the kidneys

| No. p/p | Composition SCDC | Urinary Excretion of NGAL (mcg/h) (n = 15) | Urinary NAG Excretion (mcg/h) (n = 15) |
|---|---|---|---|
| 1 | Control (colistin) | 775 ± 33 | 2578 ± 95 |
| 2 | Control (solution of normal saline) | 380* ± 25 | 300* ± 15 |
| 2 | Polifro | 577* ± 18 | 331* ± 10 |
| 3 | Colistin/Pantothenic acid/NAD | 610* ± 20 | 314* ± 8 |
| 4 | Colistin/Cyanocobalamin/Vikasol | 558* ± 19 | 370* ± 12 |
| 5 | Colistin/Cholecalciferol/Vikasol | 549* ± 18 | 394* ± 18 |
| 6 | Colistin/Cyanocobalamin/Pantothenic Acid | 570* ± 16 | 390* ± 17 |
| 7 | Colistin/Pantothenic Acid/Vikasol | 526* ± 21 | 502* ± 22 |
| 8 | Colistin/Cyanocobalamin/NAD | 598* ± 19 | 418* ± 21 |
| 9 | Colistin/Vikasol/NAD | 510* ± 22 | 405* ± 15 |
| 10 | Colistin/Cholecalciferol/NAD | 583* ± 25 | 518* ± 22 |
| 11 | Colistin/Cholecalciferol/pantothenic acid | 580* ± 19 | 505* ± 19 |

*P < 0.05

As can be seen from table 6, the differences in the groups of animals receiving only colistin and colistin compositions with different nephroprotectors are statistically significantly different. For acetylglucosaminidase, this indicator is 8 times different compared to the control of colistin. Thus, all patentable variants of pharmaceutical compositions of polymyxin with nephroprotective agents, even when using a subtoxic dose of polymyxin, reduced the nephrotoxicity of polymyxin to virtually the norm.

The invention claimed is:

1. A pharmaceutical composition with polymyxin and nephroprotectors, wherein the nephroprotectors are combinations of vitamins with a supramolecular combinatorial derivative of cyanocobalamin obtained by simultaneous acylation of the structure of cyanocobalamin with two different anhydrides and/or halogen anhydrides of monocarboxylic, dicarboxylic tricarboxylic and/or polycarboxylic acids;
wherein a molar ratio of components of the combinatorial reaction is calculated according to the formulas:

$$k = n \times (2^n - 1) \quad (1)$$

and $$m = 4 \times (3 \times 2^{n-2} - 1) \quad (2)$$

where n=number of substitutional groups in cyanocobalamin;

m=number of moles of the starting cyanocobalamin and a number of different molecules of its combinatorial derivatives after synthesis; and k=number of moles of each of two modifiers in the combinatorial synthesis reaction to obtain a maximum number of different derivatives.

2. The pharmaceutical composition according to claim 1, wherein the combination of vitamins includes cholecalciferol.

3. The pharmaceutical composition according to claim 1, wherein the composition includes vikasol.

4. The pharmaceutical composition according to claim 1, wherein the combination of vitamins also include ascorbic acid or its derivatives.

* * * * *